United States Patent [19]
Chan et al.

[11] Patent Number: 6,051,401
[45] Date of Patent: Apr. 18, 2000

[54] METHODS AND CONSTRUCTS FOR PROTEIN EXPRESSION

[75] Inventors: Sham Yuen Chan, El Sobrante; Van-Mai Tran; Shu-Lan Cheng, both of Orinda, all of Calif.

[73] Assignee: Bayer Corporation, Pittsburgh, Pa.

[21] Appl. No.: 09/124,605

[22] Filed: Jul. 28, 1998

[51] Int. Cl.[7] .......................... C12N 15/85; C12N 15/12; C12N 15/63; C12N 5/16
[52] U.S. Cl. .................... 435/69.1; 435/455; 435/320.1; 435/325
[58] Field of Search .................................. 435/69.1, 455, 435/320.1, 325; 536/23.5

[56] References Cited

U.S. PATENT DOCUMENTS

| | | | |
|---|---|---|---|
| 4,533,637 | 8/1985 | Yamane et al. | 435/371 |
| 4,560,655 | 12/1985 | Baker | 435/389 |
| 4,757,005 | 7/1988 | Chan | 435/215 |
| 4,767,704 | 8/1988 | Cleveland et al. | 435/70.2 |
| 4,816,401 | 3/1989 | Taupier et al. | 435/406 |
| 5,024,947 | 6/1991 | Inlow et al. | 435/404 |
| 5,081,035 | 1/1992 | Halberstadt et al. | 435/297.4 |
| 5,122,469 | 6/1992 | Mather et al. | 435/383 |
| 5,135,866 | 8/1992 | Heifetz et al. | 435/405 |
| 5,143,842 | 9/1992 | Ham et al. | 435/384 |
| 5,153,131 | 10/1992 | Wolf et al. | 435/401 |
| 5,530,109 | 6/1996 | Goodearl et al. | 536/23.5 |
| 5,612,213 | 3/1997 | Chan | 435/6 |
| 5,631,159 | 5/1997 | Marshall et al. | 435/383 |
| 5,854,021 | 12/1998 | Cho et al. | 435/69.1 |

FOREIGN PATENT DOCUMENTS

| | | |
|---|---|---|
| 0112174A2 | 6/1984 | European Pat. Off. . |
| 0 260 148 | 9/1987 | European Pat. Off. . |
| 0485689A1 | 5/1992 | European Pat. Off. . |
| WO 94/00140 | 1/1994 | WIPO . |
| WO 97/33978 | 9/1997 | WIPO . |

OTHER PUBLICATIONS

Lee, Chong–Chou et al.: "Human alpha2–HS–glycoprotein: the A and B chains with a connecting sequence are encoded by a single mRNA transcript.", Proc. Nat'l. Acad. Sci. USA, vol. 84, Jul. 1987 (1987–07), pp. 4403–7.

Nie, Z.:"Fetuin: its enigmatic property of growth promotion." American Journal of Physiology, vol. 32, No. 3, Sep. 1992 (1992–09), pp. C551–C562.

Gaillard, D., et al.: "Fetuin modulates growth and differentiation of Ob17 preadipose cells in serum–free hormone–supplemented medium." Biochimica et Biophysica Acta, vol. 846, 1985, pp. 185–191.

*Gene Structure and Expression*, 2$^{nd}$ Edition, J.D. Hawkins (Cambridge University Press, London, 1991).

Hedlund and Miller, "A Serum–Free Defined Medium Capable of Supporting Growth of Four Established Human Prostatic Carcinoma Cell Lines", The Prostate 24:221–228 (1994).

Dziegielewska et al., "Alpha–2–HS–glycoprotein is Expressed at High Concentration in Human Fetal Plasma and Cerebrospinal Fluid", Fetal Diagn. Ther. 1993; 8:22–27.

Jahnen–Dechent et al., "Posttranslational processing of human alpha–2–HS–glycoprotein (human fetuin)" Eur. J. Biochem. 226:59–69 (1994).

Yoshida et al., "Cystatin–like Domain of Mouse Countertrypsin, a Member of Mammalian Fetuin Family, is Responsible for the Inhibition of Trypsin" Biochemistry and Molecular Biology International 39(5):1023–1028 (Aug. 1996).

Demetriou et al., "Fetuin/alpha–2–HS–glycoprotein is a Transforming Growth Factor–B Type II Receptor Mimic and Cytokine Antagonist", J. Bio. Chem. 271(22):12755–12761 (1996).

Ohnishi et al., "Effect of phosphorylated rat fetuin on the growth of hepatocytes in primary culture in the presence of human hepatocyte–growth factor", Eur. J. Biochem. 243:753–761 (1997).

*Primary Examiner*—John S. Brusca
*Attorney, Agent, or Firm*—McDonnell Boehnen Hulbert & Berghoff

[57] ABSTRACT

The invention teaches methods, constructs and host cells for the effective expression of a desired protein in mammalian cell culture. In particular, the efficient expression of human GGF2 is taught.

25 Claims, 4 Drawing Sheets

CGAT [AACTAGCAGCATTTCCTCCAACGAGGATCCCGCAG (GTAAGAAGCTACACCGGCCAGTGGCCGGGGCC

CGATAACTAGCAGCATTTCCTCCAACGAGGATCCCGCAG(GTAAGAAGCTACACCGGCC

AGTGGCCGGGGCC

GTGGAGCCGGGGGCATCCGGTGCCTGAGACAGAGGTGCTCAAGGCAGTCTCCACCTTTT

GTCTCCCCTCTGCAG) AGAGCCACATTCTGGAA] GTT

SEQUENCE LISTING

<160> NUMBER OF SEQ ID NOS: 11

<210> SEQ ID NO 1
<211> LENGTH: 1459
<212> TYPE: DNA
<213> ORGANISM: Bovine cDNA
<220> FEATURE:
<221> NAME/KEY: CDS
<222> LOCATION: (12)..(1091)
<220> FEATURE:
<221> NAME/KEY: mat_peptide
<222> LOCATION: (66)..(1088)

<400> SEQUENCE: 1

```
gtgaagccac c atg aaa tcc ttc gtt ctg ctc ttt tgc ctg gct cag ctc         50
            Met Lys Ser Phe Val Leu Leu Phe Cys Leu Ala Gln Leu
                -15                 -10 tgg ggc tgc cac tcg atc ccg ctt gac ccg gtt gca ggt tat aag gaa          98
Trp Gly Cys His Ser Ile Pro Leu Asp Pro Val Ala Gly Tyr Lys Glu
 -5              -1   1               5                  10 ccg gcc tgt gat gac cca gac aca gag caa gca gcc ttg gct gcc gtg         146
Pro Ala Cys Asp Asp Pro Asp Thr Glu Gln Ala Ala Leu Ala Ala Val
             15                  20                  25 gac tac atc aac aag cac ctt cct cgg ggc tac aag cac acc ttg aac         194
Asp Tyr Ile Asn Lys His Leu Pro Arg Gly Tyr Lys His Thr Leu Asn
         30                  35                  40 cag att gac agt gtg aag gtg tgg ccg agg cgg ccc acg gga gag gtg         242
Gln Ile Asp Ser Val Lys Val Trp Pro Arg Arg Pro Thr Gly Glu Val
     45                  50                  55 tat gac att gaa ata gat acc ctg gaa acc acc tgc cac gta ctg gac         290
Tyr Asp Ile Glu Ile Asp Thr Leu Glu Thr Thr Cys His Val Leu Asp
 60                  65                  70                  75 ccc acg ccc ctg gcg aac tgc agc gtg agg cag cag acg cag cac gcg         338
Pro Thr Pro Leu Ala Asn Cys Ser Val Arg Gln Gln Thr Gln His Ala
                 80                  85                  90 gtg gaa gga gac tgc gat atc cac gtg ctg aaa caa gat ggc cag ttt         386
Val Glu Gly Asp Cys Asp Ile His Val Leu Lys Gln Asp Gly Gln Phe
             95                 100                 105 tcc gtg ctg ttt aca aaa tgt gat tcc agt cca gat tcc gcc gag gac         434
Ser Val Leu Phe Thr Lys Cys Asp Ser Ser Pro Asp Ser Ala Glu Asp
        110                 115                 120 gtg cgc aag ttg tgc cca gac tgc ccc ctg ctg gcg cca ctc aac gac         482
Val Arg Lys Leu Cys Pro Asp Cys Pro Leu Leu Ala Pro Leu Asn Asp
    125                 130                 135 agc cgg gtg gtg cac gca gtg gag gtc gcg ctg gct acc ttc aat gcc         530
Ser Arg Val Val His Ala Val Glu Val Ala Leu Ala Thr Phe Asn Ala
140                 145                 150                 155 gag agc aac ggc tcc tac tta cag ctg gtg gaa att tct cgg gct caa         578
Glu Ser Asn Gly Ser Tyr Leu Gln Leu Val Glu Ile Ser Arg Ala Gln
                160                 165                 170 ttt gtg cct ctt cca gtt tct gtc tct gtg gag ttt gca gtg gct gct         626
Phe Val Pro Leu Pro Val Ser Val Ser Val Glu Phe Ala Val Ala Ala
            175                 180                 185 act gac tgt att gct aaa gaa gtc gta gat cca acc aag tgc aac cta         674
Thr Asp Cys Ile Ala Lys Glu Val Val Asp Pro Thr Lys Cys Asn Leu
        190                 195                 200 ctg gca gaa aag caa tat ggc ttc tgt aag ggg tca gtc att cag aaa         722
Leu Ala Glu Lys Gln Tyr Gly Phe Cys Lys Gly Ser Val Ile Gln Lys
    205                 210                 215 gct ctt ggt ggg gag gac gtc aga gtg act tgc acg ttg ttc caa acg         770
Ala Leu Gly Gly Glu Asp Val Arg Val Thr Cys Thr Leu Phe Gln Thr
```

-continued

```
Ala Leu Gly Gly Glu Asp Val Arg Val Thr Cys Thr Leu Phe Gln Thr
220                 225                 230                 235 cag cct gtg att ccg cag ccc cag ccc gac ggc gcc gag gct gag gcc      818
Gln Pro Val Ile Pro Gln Pro Gln Pro Asp Gly Ala Glu Ala Glu Ala
                240                 245                 250 cca agc gct gtg ccg gac gca gct ggg cct acg cct tct gca gct ggc      866
Pro Ser Ala Val Pro Asp Ala Ala Gly Pro Thr Pro Ser Ala Ala Gly
                255                 260                 265 ccg ccc gtg gcc tcc gtg gtg gtg ggg cca agc gtg gta gca gtt ccc      914
Pro Pro Val Ala Ser Val Val Val Gly Pro Ser Val Val Ala Val Pro
            270                 275                 280 ctg ccg ctg cac cga gca cac tac gac ttg cgc cac act ttc tcc ggg      962
Leu Pro Leu His Arg Ala His Tyr Asp Leu Arg His Thr Phe Ser Gly
        285                 290                 295 gtg gcc tca gtg gag tca tcc tcg gga gaa gcg ttc cac gtg ggc aaa     1010
Val Ala Ser Val Glu Ser Ser Ser Gly Glu Ala Phe His Val Gly Lys
300                 305                 310                 315 aca ccc ata gtg ggg cag cct agc att cct gga ggt cca gtc cgc ctt     1058
Thr Pro Ile Val Gly Gln Pro Ser Ile Pro Gly Gly Pro Val Arg Leu
                320                 325                 330 tgc cca ggg aga atc aga tac ttc aag atc tag aagatggtcg gagatgagat  1111
Cys Pro Gly Arg Ile Arg Tyr Phe Lys Ile
                335                 340 ggtttggcac agagaataca gctatcattt tgtccaagtc atgggtatgg gtagggctt   1171 tgtctgctct ggaagcaagt gctgcctatg gtctagatta atgtcaggtc ttgagtccca  1231
acttctcatc cttccaagga caggagcaga ggaggtgcta gtgatgtttg atggaacata  1291
aagtcagcag cttgattgtc atggctttga tgtaagccac caccactgtg ttctctacct  1351
tctcttgacc tcacaaaagt aattggaact gtgactttga aaggtgctct tgccaagttt  1411
atatctactt gtcattaaaa atgctctaat aaagaaggtt ctaagctg               1459

<210> SEQ ID NO 2
<211> LENGTH: 359
<212> TYPE: PRT
<213> ORGANISM: Bovine cDNA

<400> SEQUENCE: 2

Met Lys Ser Phe Val Leu Leu Phe Cys Leu Ala Gln Leu Trp Gly Cys
1               5                   10                  15

His Ser Ile Pro Leu Asp Pro Val Ala Gly Tyr Lys Glu Pro Ala Cys
                20                  25                  30

Asp Asp Pro Asp Thr Glu Gln Ala Ala Leu Ala Ala Val Asp Tyr Ile
            35                  40                  45

Asn Lys His Leu Pro Arg Gly Tyr Lys His Thr Leu Asn Gln Ile Asp
        50                  55                  60

Ser Val Lys Val Trp Pro Arg Arg Pro Thr Gly Glu Val Tyr Asp Ile
65              70                  75                  80

Glu Ile Asp Thr Leu Glu Thr Thr Cys His Val Leu Asp Pro Thr Pro
                85                  90                  95

Leu Ala Asn Cys Ser Val Arg Gln Gln Thr Gln His Ala Val Glu Gly
                100                 105                 110

Asp Cys Asp Ile His Val Leu Lys Gln Asp Gly Gln Phe Ser Val Leu
            115                 120                 125

Phe Thr Lys Cys Asp Ser Ser Pro Asp Ser Ala Glu Asp Val Arg Lys
        130                 135                 140

Leu Cys Pro Asp Cys Pro Leu Leu Ala Pro Leu Asn Asp Ser Arg Val
```

```
145                 150                 155                 160
    Val His Ala Val Glu Val Ala Leu Ala Thr Phe Asn Ala Glu Ser Asn
                    165                 170                 175

Gly Ser Tyr Leu Gln Leu Val Glu Ile Ser Arg Ala Gln Phe Val Pro
                180                 185                 190

Leu Pro Val Ser Val Ser Val Glu Phe Ala Val Ala Thr Asp Cys
            195                 200                 205

Ile Ala Lys Glu Val Val Asp Pro Thr Lys Cys Asn Leu Leu Ala Glu
        210                 215                 220

Lys Gln Tyr Gly Phe Cys Lys Gly Ser Val Ile Gln Lys Ala Leu Gly
    225                 230                 235                 240

Gly Glu Asp Val Arg Val Thr Cys Thr Leu Phe Gln Thr Gln Pro Val
                    245                 250                 255

Ile Pro Gln Pro Gln Pro Asp Gly Ala Glu Ala Glu Ala Pro Ser Ala
                260                 265                 270

Val Pro Asp Ala Ala Gly Pro Thr Pro Ser Ala Ala Gly Pro Pro Val
            275                 280                 285

Ala Ser Val Val Val Gly Pro Ser Val Val Ala Val Pro Leu Pro Leu
        290                 295                 300

His Arg Ala His Tyr Asp Leu Arg His Thr Phe Ser Gly Val Ala Ser
    305                 310                 315                 320

Val Glu Ser Ser Gly Glu Ala Phe His Val Gly Lys Thr Pro Ile
                    325                 330                 335

Val Gly Gln Pro Ser Ile Pro Gly Gly Pro Val Arg Leu Cys Pro Gly
                340                 345                 350

Arg Ile Arg Tyr Phe Lys Ile
            355

<210> SEQ ID NO 3
<211> LENGTH: 1538
<212> TYPE: DNA
<213> ORGANISM: Homo sapiens
<220> FEATURE:
<221> NAME/KEY: CDS
<222> LOCATION: (49)..(1149)

<400> SEQUENCE: 3
cctccaacca cctgcacgcc tgcctgccag ggcctctctg gggcagcc atg aag tcc        57
                                                    Met Lys Ser
                                                      1 ctc gtc ctg ctc ctt tgt ctt gct cag ctc tgg ggc tgc cac tca gcc       105
Leu Val Leu Leu Leu Cys Leu Ala Gln Leu Trp Gly Cys His Ser Ala
      5                  10                  15 cca cat ggc cca ggg ctg att tat aga caa ccg aac tgc gat gat cca       153
Pro His Gly Pro Gly Leu Ile Tyr Arg Gln Pro Asn Cys Asp Asp Pro
 20                  25                  30                  35 gaa act gag gaa gca gct ctg gtg gct ata gac tac atc aat caa aac       201
Glu Thr Glu Glu Ala Ala Leu Val Ala Ile Asp Tyr Ile Asn Gln Asn
                 40                  45                  50 ctt cct tgg gga tac aaa cac acc ttg aac cag att gat gaa gta aag       249
Leu Pro Trp Gly Tyr Lys His Thr Leu Asn Gln Ile Asp Glu Val Lys
             55                  60                  65 gtg tgg cct cag cag ccc tcc gga gag ctg ttt gag att gaa ata gac       297
Val Trp Pro Gln Gln Pro Ser Gly Glu Leu Phe Glu Ile Glu Ile Asp
         70                  75                  80 acc ctg gaa acc acc tgc cat gtg ctg gac ccc acc cct gtg gca aga       345
Thr Leu Glu Thr Thr Cys His Val Leu Asp Pro Thr Pro Val Ala Arg
     85                  90                  95
```

-continued

```
tgc agc gtg agg cag ctg aag gag cat gct gtc gaa gga gac tgt gat      393
Cys Ser Val Arg Gln Leu Lys Glu His Ala Val Glu Gly Asp Cys Asp
100                 105                 110                 115 ttc cag ctg ttg aaa cta gat ggc aag ttt tcc gtg gta tac gca aaa      441
Phe Gln Leu Leu Lys Leu Asp Gly Lys Phe Ser Val Val Tyr Ala Lys
                120                 125                 130 tgt gat tcc agt cca gac tca gcc gag gac gtg cgc aag gtg tgc caa      489
Cys Asp Ser Ser Pro Asp Ser Ala Glu Asp Val Arg Lys Val Cys Gln
            135                 140                 145 gac tgc ccc ctg ctg gcc ccg ctg aac gac acc agg gtg gtg cac gcc      537
Asp Cys Pro Leu Leu Ala Pro Leu Asn Asp Thr Arg Val Val His Ala
        150                 155                 160 gcg aaa gct gcc ctg gcc gcc ttc aac gct cag aac aac ggc tcc aat      585
Ala Lys Ala Ala Leu Ala Ala Phe Asn Ala Gln Asn Asn Gly Ser Asn
165                 170                 175 ttt cag ctg gag gaa att tcc cgg gct cag ctt gtg ccc ctc cca cct      633
Phe Gln Leu Glu Glu Ile Ser Arg Ala Gln Leu Val Pro Leu Pro Pro
180                 185                 190                 195 tct acc tat gtg gag ttt aca gtg tct ggc act gac tgt gtt gct aaa      681
Ser Thr Tyr Val Glu Phe Thr Val Ser Gly Thr Asp Cys Val Ala Lys
                200                 205                 210 gag gcc aca gag gca gcc aag tgt aac ctg ctg gca gaa aag caa tat      729
Glu Ala Thr Glu Ala Ala Lys Cys Asn Leu Leu Ala Glu Lys Gln Tyr
            215                 220                 225 ggc ttt tgt aag gca aca ctc agt gag aag ctt ggt ggg gca gag gtt      777
Gly Phe Cys Lys Ala Thr Leu Ser Glu Lys Leu Gly Gly Ala Glu Val
        230                 235                 240 gca gtg acc tgc acg gtg ttc caa aca cag ccc gtg acc tca cag ccc      825
Ala Val Thr Cys Thr Val Phe Gln Thr Gln Pro Val Thr Ser Gln Pro
245                 250                 255 caa cca gaa ggt gcc aat gaa gca gtc ccc acc ccc gtg gtg gac cca      873
Gln Pro Glu Gly Ala Asn Glu Ala Val Pro Thr Pro Val Val Asp Pro
260                 265                 270                 275 gat gca cct ccg tcc cct cca ctt ggc gca cct gga ctc cct cca gct      921
Asp Ala Pro Pro Ser Pro Pro Leu Gly Ala Pro Gly Leu Pro Pro Ala
                280                 285                 290 ggc tca ccc cca gac tcc cat gtg tta ctg gca gct cct cca gga cac      969
Gly Ser Pro Pro Asp Ser His Val Leu Leu Ala Ala Pro Pro Gly His
            295                 300                 305 cag ttg cac cgg gcg cac tac gac ctg cgc cac acc ttc atg ggt gtg     1017
Gln Leu His Arg Ala His Tyr Asp Leu Arg His Thr Phe Met Gly Val
        310                 315                 320 gtc tca ttg ggg tca ccc tca gga gaa gtg tcg cac ccc cgg aaa aca     1065
Val Ser Leu Gly Ser Pro Ser Gly Glu Val Ser His Pro Arg Lys Thr
325                 330                 335 cgc aca gtg gtg cag cct agt gtt ggt gct gct gct ggg cca gtg gtt     1113
Arg Thr Val Val Gln Pro Ser Val Gly Ala Ala Ala Gly Pro Val Val
340                 345                 350                 355 cct cca tgt ccg ggg agg atc aga cac ttc aag gtc taggctagac          1159
Pro Pro Cys Pro Gly Arg Ile Arg His Phe Lys Val
                360                 365 atggcagaga tgaggaggtt tggcacagaa acatagcca  ccattttgtc  caagcctggg  1219
catgggtggg gggccttgtc tgctggccac gcaagtgtca catgcgatct acattaatat  1279
caagtcttga ctccctactt cccgtcattc ctcacaggac agaagcagag tgggtggtgg  1339
ttatgtttga cagaaggcat taggttgaca acttgtcatg attttgacgg taagccacca  1399
tgattgtgtt ctctgcctct ggttgacctt acaaaaacca ttggaactgt gactttgaaa  1459
```

-continued

```
ggtgctcttg ctaagcttat atgtgcctgt taatgaaagt gcctgaaaga ccttccttaa      1519
taaagaaggt tctaagctg                                                   1538
```

```
<210> SEQ ID NO 4
<211> LENGTH: 367
<212> TYPE: PRT
<213> ORGANISM: Homo sapiens

<400> SEQUENCE: 4
```

```
Met Lys Ser Leu Val Leu Leu Cys Leu Ala Gln Leu Trp Gly Cys
 1               5                  10                  15

His Ser Ala Pro His Gly Pro Gly Leu Ile Tyr Arg Gln Pro Asn Cys
                20                  25                  30

Asp Asp Pro Glu Thr Glu Glu Ala Ala Leu Val Ala Ile Asp Tyr Ile
            35                  40                  45

Asn Gln Asn Leu Pro Trp Gly Tyr Lys His Thr Leu Asn Gln Ile Asp
        50                  55                  60

Glu Val Lys Val Trp Pro Gln Gln Pro Ser Gly Glu Leu Phe Glu Ile
 65                 70                  75                  80

Glu Ile Asp Thr Leu Glu Thr Thr Cys His Val Leu Asp Pro Thr Pro
                85                  90                  95

Val Ala Arg Cys Ser Val Arg Gln Leu Lys Glu His Ala Val Glu Gly
            100                 105                 110

Asp Cys Asp Phe Gln Leu Leu Lys Leu Asp Gly Lys Phe Ser Val Val
        115                 120                 125

Tyr Ala Lys Cys Asp Ser Ser Pro Asp Ser Ala Glu Asp Val Arg Lys
    130                 135                 140

Val Cys Gln Asp Cys Pro Leu Leu Ala Pro Leu Asn Asp Thr Arg Val
145                 150                 155                 160

Val His Ala Ala Lys Ala Ala Leu Ala Ala Phe Asn Ala Gln Asn Asn
                165                 170                 175

Gly Ser Asn Phe Gln Leu Glu Glu Ile Ser Arg Ala Gln Leu Val Pro
            180                 185                 190

Leu Pro Pro Ser Thr Tyr Val Glu Phe Thr Val Ser Gly Thr Asp Cys
        195                 200                 205

Val Ala Lys Glu Ala Thr Glu Ala Ala Lys Cys Asn Leu Leu Ala Glu
    210                 215                 220

Lys Gln Tyr Gly Phe Cys Lys Ala Thr Leu Ser Glu Lys Leu Gly Gly
225                 230                 235                 240

Ala Glu Val Ala Val Thr Cys Thr Val Phe Gln Thr Gln Pro Val Thr
                245                 250                 255

Ser Gln Pro Gln Pro Glu Gly Ala Asn Glu Ala Val Pro Thr Pro Val
            260                 265                 270

Val Asp Pro Asp Ala Pro Pro Ser Pro Pro Leu Gly Ala Pro Gly Leu
        275                 280                 285

Pro Pro Ala Gly Ser Pro Pro Asp Ser His Val Leu Leu Ala Ala Pro
    290                 295                 300

Pro Gly His Gln Leu His Arg Ala His Tyr Asp Leu Arg His Thr Phe
305                 310                 315                 320

Met Gly Val Val Ser Leu Gly Ser Pro Ser Gly Glu Val Ser His Pro
                325                 330                 335

Arg Lys Thr Arg Thr Val Val Gln Pro Ser Val Gly Ala Ala Ala Gly
            340                 345                 350

Pro Val Val Pro Pro Cys Pro Gly Arg Ile Arg His Phe Lys Val
```

```
                         355                 360                 365

<210> SEQ ID NO 5
<211> LENGTH: 1200
<212> TYPE: DNA
<213> ORGANISM: Artificial Sequence
<220> FEATURE:
<223> OTHER INFORMATION: Description of Artificial Sequence:Human
      ortholog
<220> FEATURE:
<221> NAME/KEY: CDS
<222> LOCATION: (49)..(1149)

<400> SEQUENCE: 5
cctccaacca cctgcacgcc tgcctgccag ggcctctctg gggcagcc atg aag tcc        57
                                                    Met Lys Ser
                                                      1 ctc gtc ctg ctc ctt tgt ctt gct cag ctc tgg ggc tgc cac tca gcc       105
Leu Val Leu Leu Leu Cys Leu Ala Gln Leu Trp Gly Cys His Ser Ala
          5                  10                  15 cca cat ggc cca ggg ctg att tat aga caa ccg aac tgc gat gat cca       153
Pro His Gly Pro Gly Leu Ile Tyr Arg Gln Pro Asn Cys Asp Asp Pro
 20                  25                  30                  35 gaa act gag gaa gca gct ctg gtg gct ata gac tac atc aat caa aac       201
Glu Thr Glu Glu Ala Ala Leu Val Ala Ile Asp Tyr Ile Asn Gln Asn
                 40                  45                  50 ctt cct tgg gga tac aaa cac acc ttg aac cag att gat gaa gta aag       249
Leu Pro Trp Gly Tyr Lys His Thr Leu Asn Gln Ile Asp Glu Val Lys
             55                  60                  65 gtg tgg cct cag cag ccc tcc gga gag ctg ttt gag att gaa ata gac       297
Val Trp Pro Gln Gln Pro Ser Gly Glu Leu Phe Glu Ile Glu Ile Asp
         70                  75                  80 acc ctg gaa acc acc tgc cat gtg ctg gac ccc acc cct gtg gca aga       345
Thr Leu Glu Thr Thr Cys His Val Leu Asp Pro Thr Pro Val Ala Arg
     85                  90                  95 tgc agc gtg agg cag ctg aag gag cat gct gtc gaa gga gac tgt gat       393
Cys Ser Val Arg Gln Leu Lys Glu His Ala Val Glu Gly Asp Cys Asp
100                 105                 110                 115 ttc cag ctg ttg aaa cta gat ggc aag ttt tcc gtg gta tac gca aaa       441
Phe Gln Leu Leu Lys Leu Asp Gly Lys Phe Ser Val Val Tyr Ala Lys
                120                 125                 130 tgt gat tcc agt cca gac tca gcc gag gac gtg cgc aag gtg tgc caa       489
Cys Asp Ser Ser Pro Asp Ser Ala Glu Asp Val Arg Lys Val Cys Gln
            135                 140                 145 gac tgc ccc ctg ctg gcc ccg ctg aac gac acc agg gtg gtg cac gcc       537
Asp Cys Pro Leu Leu Ala Pro Leu Asn Asp Thr Arg Val Val His Ala
        150                 155                 160 gcg aaa gct gcc ctg gcc gcc ttc aac gct cag aac aac ggc tcc aat       585
Ala Lys Ala Ala Leu Ala Ala Phe Asn Ala Gln Asn Asn Gly Ser Asn
    165                 170                 175 ttt cag ctg gag gaa att tcc cgg gct cag ctt gtg ccc ctc cca cct       633
Phe Gln Leu Glu Glu Ile Ser Arg Ala Gln Leu Val Pro Leu Pro Pro
180                 185                 190                 195 tct acc tat gtg gag ttt aca gtg tct ggc act gac tgt gtt gct aaa       681
Ser Thr Tyr Val Glu Phe Thr Val Ser Gly Thr Asp Cys Val Ala Lys
                200                 205                 210 gag gcc aca gag gca gcc aag tgt aac ctg ctg gca gaa aag caa tat       729
Glu Ala Thr Glu Ala Ala Lys Cys Asn Leu Leu Ala Glu Lys Gln Tyr
            215                 220                 225 ggc ttt tgt aag gca aca ctc agt gag aag ctt ggt ggg gca gag gtt       777
Gly Phe Cys Lys Ala Thr Leu Ser Glu Lys Leu Gly Gly Ala Glu Val
        230                 235                 240
```

```
gca gtg acc tgc atg gtg ttc caa aca cag ccc gtg agc tca cag ccc      825
Ala Val Thr Cys Met Val Phe Gln Thr Gln Pro Val Ser Ser Gln Pro
    245                 250                 255 caa cca gaa ggt gcc aat gaa gca gtc ccc acc ccc gtg gtg gac cca      873
Gln Pro Glu Gly Ala Asn Glu Ala Val Pro Thr Pro Val Val Asp Pro
260                 265                 270                 275 gat gca cct ccg tcc cct cca ctt ggc gca cct gga ctc cct cca gct      921
Asp Ala Pro Pro Ser Pro Pro Leu Gly Ala Pro Gly Leu Pro Pro Ala
                280                 285                 290 ggc tca ccc cca gac tcc cat gtg tta ctg gca gct cct gga cac          969
Gly Ser Pro Pro Asp Ser His Val Leu Leu Ala Ala Pro Gly His
            295                 300                 305 cag ttg cac cgg gcg cac tac gac ctg cgc cac acc ttc atg ggt gtg     1017
Gln Leu His Arg Ala His Tyr Asp Leu Arg His Thr Phe Met Gly Val
    310                 315                 320 gtc tca ttg ggg tca ccc tca gga gaa gtg tcg cac ccc cgg aaa aca     1065
Val Ser Leu Gly Ser Pro Ser Gly Glu Val Ser His Pro Arg Lys Thr
325                 330                 335 cgc aca gtg gtg cag cct agt gtt ggt gct gct gct ggg cca gtg gtt     1113
Arg Thr Val Val Gln Pro Ser Val Gly Ala Ala Ala Gly Pro Val Val
340                 345                 350                 355 cct cca tgt ccg ggg agg atc aga cac ttc aag gtc taggctagac          1159
Pro Pro Cys Pro Gly Arg Ile Arg His Phe Lys Val
                360                 365 atggcagaga tgaggaggtt tggcacagaa aacatagcca c                       1200

<210> SEQ ID NO 6
<211> LENGTH: 367
<212> TYPE: PRT
<213> ORGANISM: Artificial Sequence

<400> SEQUENCE: 6

Met Lys Ser Leu Val Leu Leu Cys Leu Ala Gln Leu Trp Gly Cys
 1               5                  10                  15

His Ser Ala Pro His Gly Pro Gly Leu Ile Tyr Arg Gln Pro Asn Cys
            20                  25                  30

Asp Asp Pro Glu Thr Glu Glu Ala Ala Leu Val Ala Ile Asp Tyr Ile
        35                  40                  45

Asn Gln Asn Leu Pro Trp Gly Tyr Lys His Thr Leu Asn Gln Ile Asp
    50                  55                  60

Glu Val Lys Val Trp Pro Gln Gln Pro Ser Gly Glu Leu Phe Glu Ile
65                  70                  75                  80

Glu Ile Asp Thr Leu Glu Thr Thr Cys His Val Leu Asp Pro Thr Pro
                85                  90                  95

Val Ala Arg Cys Ser Val Arg Gln Leu Lys Glu His Ala Val Glu Gly
            100                 105                 110

Asp Cys Asp Phe Gln Leu Leu Lys Leu Asp Gly Lys Phe Ser Val Val
        115                 120                 125

Tyr Ala Lys Cys Asp Ser Ser Pro Asp Ser Ala Glu Asp Val Arg Lys
    130                 135                 140

Val Cys Gln Asp Cys Pro Leu Leu Ala Pro Leu Asn Asp Thr Arg Val
145                 150                 155                 160

Val His Ala Ala Lys Ala Ala Leu Ala Ala Phe Asn Ala Gln Asn Asn
                165                 170                 175

Gly Ser Asn Phe Gln Leu Glu Glu Ile Ser Arg Ala Gln Leu Val Pro
            180                 185                 190
```

```
Leu Pro Pro Ser Thr Tyr Val Glu Phe Thr Val Ser Gly Thr Asp Cys
            195                 200                 205

Val Ala Lys Glu Ala Thr Glu Ala Ala Lys Cys Asn Leu Leu Ala Glu
210                 215                 220

Lys Gln Tyr Gly Phe Cys Lys Ala Thr Leu Ser Glu Lys Leu Gly Gly
225                 230                 235                 240

Ala Glu Val Ala Val Thr Cys Met Val Phe Gln Thr Gln Pro Val Ser
                245                 250                 255

Ser Gln Pro Gln Pro Glu Gly Ala Asn Glu Ala Val Pro Thr Pro Val
            260                 265                 270

Val Asp Pro Asp Ala Pro Pro Ser Pro Pro Leu Gly Ala Pro Gly Leu
            275                 280                 285

Pro Pro Ala Gly Ser Pro Pro Asp Ser His Val Leu Leu Ala Ala Pro
    290                 295                 300

Pro Gly His Gln Leu His Arg Ala His Tyr Asp Leu Arg His Thr Phe
305                 310                 315                 320

Met Gly Val Val Ser Leu Gly Ser Pro Ser Gly Glu Val Ser His Pro
                325                 330                 335

Arg Lys Thr Arg Thr Val Val Gln Pro Ser Val Gly Ala Ala Ala Gly
                340                 345                 350

Pro Val Val Pro Pro Cys Pro Gly Arg Ile Arg His Phe Lys Val
            355                 360                 365

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Fetuin PCR
      primer

<400> SEQUENCE: 7
cctccaacca cctgcacgcc                                                20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:Fetuin PCR
      primer

<400> SEQUENCE: 8
ggcacagaaa acatagccac                                                20

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:MIS PCR
      primer

<400> SEQUENCE: 9
ggatcgataa ctagcagcat ttcct                                          25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:MIS PCR
```

```
    primer

<400> SEQUENCE: 10
gggttaactt ccagaatgtg gctct                                            25

<210> SEQ ID NO 11
<211> LENGTH: 236
<212> TYPE: DNA
<213> ORGANISM: Artificial Sequence
<220> FEATURE:
<223> OTHER INFORMATION: Description of Artificial Sequence: EBV derived
      MIS

<400> SEQUENCE: 11
cgataactag cagcatttcc tccaacgagg atcccgcagg taagaagcta caccggccag      60
tggccggggc ccgataacta gcagcatttc ctccaacgag gatcccgcag gtaagaagct     120
acaccggcca gtggccgggg ccgtggagcc gggggcatcc ggtgcctgag acagaggtgc     180
tcaaggcagt ctccaccttt tgtctcccct ctgcagagag ccacattctg gaagtt        236
```

METHODS AND CONSTRUCTS FOR PROTEIN EXPRESSION

FIELD OF THE INVENTION

The invention relates to the field of gene expression technology and the production of protein using transformed host cells and recombinant DNA vectors.

In particular, the invention relates to the area of efficient protein production in transformed mammalian host cells, and methods, constructs and host cells for effecting such.

BACKGROUND OF INVENTION

Efficient means of expressing cloned genes as protein product are an essential tool for the identification and characterization of cloned genes, the generation of large quantities of protein for structure-function analysis, and the production of protein for use in medicinal pharmaceutical preparations.

Protein expression systems are described in the literature, and for example as found in such reference works as *Gene Expression Technology*, Methods in Enzymology Vol. 185 (ed. David Goeddel et al., Academic Press, Inc., London, 1991), *Gene Structure and Expression*, $2^{nd}$ Edition, J. D. Hawkins (Cambridge University Press, London, 1991) and their cited references. The expression of simple proteins can be routinely accomplished by using suitable *Escherichia coli* expression systems, however, these systems are typically inadequate for the expression of complex mammalian proteins. Mammalian expression systems have been developed for use in protein expression systems, however these systems have complex culture media requirements, and are extremely difficult and costly to maintain as large-scale, long-term culture systems.

Adaptation of protein producing cell lines to low-protein or serum-free media has been one method of simplifying the final purification of desired protein product, as described for example in U.S. Pat. No. 4,757,005 (incorporated by reference in its entirety). Many improved nutrient medium and serum free medium have been described in U.S. Pat. Nos. 5,143,842; 4,560,655; 5,024,947; 4,533,637; 4,767,704; 4,816,401; 5,631,159; 5,135,866 (these and all subsequently identified patents are hereby incorporated by reference in their entirety) and the literature, as in for example Hedlund and Miller "A Serum-Free Defined Medium Capable of supporting growth of four established human prostatic carcinoma cell lines" The Prostate 24:221–228 (1994). Methods for the culture of mammalian cells have also been described, as in U.S. Pat. No. 5,122,469 and the literature. Large-scale culture and protein production techniques and apparatus have also been described, as in U.S. Pat. Nos. 5,081,035 and 5,153,131, and the literature.

Thus it is well recognized in the art that there is a need for mammalian protein expression systems and methods, and in particular protein-free mammalian protein production systems suitable for large-scale protein production. This is especially true given the recent discovery of and fear of prion transmission and related disease from the use of mammalian protein supplements, especially sheep and bovine protein products.

The present invention addresses this need and describes the unexpected discovery that mammalian host cells can be adapted for efficient protein expression of a desired protein, by the transformation or co-transformation of the host cell for the expression of an additional protein, said additional protein being either alpha-2-HS-glycoprotein, or a mammalian fetuin protein.

For simplicity, in the remainder of the specification, unless otherwise identified, the term "fetuin" shall mean human alpha-2-HS-glycoprotein (AHSG), and all mammalian fetuin protein equivalents, including and not limited to bovine, murine, porcine, equine, and rat, their orthologs and derivatives.

Fetuin was the first fetal protein characterized in fetal calf serum, and was found to be homologous to human alpha-2-HS-glycoprotein (Dziegielewska et al., 1993, "alpha-2-HS-glycoprotein is expressed at high concentration in human fetal plasma and cerebrospinal fluid", Fetal Diagn. Ther. 8:22–27). The alpha-2-HS-glycoprotein is predominantly produced by liver hepatocytes, and is thought to undergo post-translational modification (Jahnen-Dechent et al., 1994, "Posttranslational processing of human alpha-2-HS-glycoprotein (human fetuin)" Eur. J. Biochem. 226:59–69). The cystatin-like domain of murine countertrypin has been found to inhibit trypsin (Yoshida et al., 1996, "Cystatin-like domain of mouse countertrypsin, a member of mammalian fetuin family, is responsible for the inhibition of trypsin" Biochemistry and Molecular Biology International 39(5):1023–1028). Fetuin/alpha-2-HS-glycoprotein has been found to be expressed during embryogenesis and found to promote bone remodeling and stimulate cell proliferation, as well as to act as an antagonist to the antiproliferative action of transforming growth factor beta1 (TGF-β1) (Demetriou et al., 1996, "Fetuin/alpha-2-HS-glycoprotein is a transforming growth factor-β Type II receptor mimic and cytokine antagonist", J. Bio. Chem. 271(22):12755–12761). Rat phosphofetuin (phosphorylated fetuin) was found to modulate hepatocyte HGF activity (Ohnishi et al., 1997, "Effect of phosphorylated rat fetuin on the growth of hepatocytes in primary culture in the presence of human hepatocyte-growth factor", Eur. J. Biochem. 243:753–761).

Fetuin, as a component of fetal calf serum, has been identified as a component of basic culture media, as in for example, U.S. Pat. Nos. 4,757,005, and 5,143,842. However, it is the present invention which discovered that the transformation of host cells to express fetuin in conjunction with expression of a desired protein product allows for the efficient expression of the desired protein, and for the simplified transition of the transformed host cells to a serum-free or reduced protein culture system, allowing for large-scale production of protein.

BRIEF DESCRIPTION OF THE INVENTION

The present invention encompasses the fundamental discovery that efficient expression of a desired protein can be accomplished by using a mammalian host cell that is also expressing fetuin protein. Such a transformed host cell expressing fetuin and a desired protein is thus suitable for adaptation to serum-free, or low protein large-scale culture protein production. The fetuin of the present invention encompasses human alpha-2-HS-glycoprotein (AHSG), and all mammalian fetuin protein equivalents, including and not limited to bovine, murine, porcine, equine, and rat, their orthologs and derivatives. In a preferred embodiment of the invention, the fetuin is either human or bovine, their orthologs and derivatives.

The instant invention encompasses efficient expression of a desired protein in all mammalian cell culture systems, including and not limited to large-scale, serum-free, hollow-fiber, suspension culture, adherent culture, fermentation culture, and small-scale protein expression. In particular, the instant invention is directed to low-protein or serum-free expression systems.

The mammalian host cells suitable for use in the present invention include, and are not limited to CHO cells, HeLa cells, and other mammalian cells adapted for expression of recombinant proteins. The mammalian host cells of the present invention can be cells which normally express fetuin, and so are selected for such expression, selected for higher expression, or adapted for such expression. Such pre-existing fetuin expression cells can be modified to express higher levels of fetuin than normally produced, via genetic manipulation of the endogenous genome or transfection with one or more suitable expression vector(s). The mammalian host cells of the present invention can be normally non-expressing for fetuin, and following the teaching of the present invention, transformed to express fetuin. The transformation of suitable host cells for the expression of fetuin can be accomplished by either transformation with a suitable expression vector containing an exogenous fetuin gene, or by adaptation of the host cell to express endogenous fetuin gene.

The desired protein product can be expressed from the fetuin adapted host cell by means of standard expression vectors, or by the manipulation of the host cell genome to integrate and express desired protein. It is also possible to construct an expression vector which expresses both fetuin and the desired protein. In such a case, the fetuin gene and the gene for the desired protein can be under the control of either the same or different promoter/enhancer systems. It is not beyond the scope of the present invention to produce fetuin-desired protein fusion products for expression.

One particular embodiment of the present invention encompasses an improved mammalian expression vector for recombinant human glial growth factor 2 (GGF2), the GGF2 cell lines CHO (dhfr⁻/GGF2) transformed with such a vector, CHO(dhfr⁻/α2HSGP/GGF2) that are capable of stable and augmented secretion levels of GGF2, and a protein-free production process for GGF2 by continuously perfusing the cells of the invention in a fermenter.

Thus the present invention encompasses a method for producing a desired protein from a recombinant DNA expression vector in a mammalian host cell, said method comprising transforming a mammalian host cell with an expression vector containing an expressible mammalian fetuin gene, transforming the same mammalian host cell with an expression vector containing an expressible gene which encodes for a desired protein, expanding said transformed host cells in culture, and isolating said desired protein from said culture. The present invention further contemplates the method wherein said vector containing an expressible mammalian fetuin gene, or said expression vector containing an expressible gene which encodes for a desired protein also contains a gene encoding for a selectable marker. It is also contemplated that said expression vector containing an expressible mammalian fetuin gene also contains an expressible gene which encodes for a desired protein. The present invention encompasses an expression vector comprising, a promoter, a coding sequence for fetuin, said coding sequence being operably linked to the promoter, an intronic sequence, the intronic sequence being downstream of the promoter and upstream of the fetuin coding sequence, the intronic sequence comprising two identical donor sites and one acceptor site, and a coding sequence of a heterologous protein, the coding sequence being operably linked to a promoter.

It is contemplated that the order of transformation of a target host cell, when using two expression vectors, can be such that said mammalian host cell is first transformed with an expression vector containing an expressible mammalian fetuin gene. It is thus contemplated by the methods of the present invention that a target host cell is first transformed with an expression vector containing an expressible gene which encodes for a desired protein.

Thus the invention encompasses a method for producing a transformed mammalian host cell for production of a desired protein from a recombinant DNA expression vector in said mammalian host cell, said method comprising transforming a mammalian host cell with an expression vector containing an expressible mammalian fetuin gene, and transforming the same mammalian host cell with an expression vector containing an expressible gene which encodes for a desired protein. Also contemplated is such a method wherein said vector containing an expressible mammalian fetuin gene, or said expression vector containing an expressible gene which encodes for a desired protein also contains a gene encoding for a selectable marker.

In one further embodiment of the invention, the method for producing a host cell of the invention is contemplated wherein said expression vector containing an expressible mammalian fetuin gene also contains an expressible gene which encodes for a desired protein, and wherein said expression vector contains a gene which encodes for a selectable marker. The method of the invention for producing transformed host cells contemplates a method where said mammalian host cell is first transformed with an expression vector containing an expressible mammalian fetuin gene, or a method where said mammalian host cell is first transformed with an expression vector containing an expressible gene which encodes for a desired protein.

A further embodiment of the invention are host cells produced by the methods of the invention. In particular, the invention encompasses a mammalian host cell for the expression of a desired protein in cell culture, wherein said host cell is transformed with an expression vector containing an expressible mammalian fetuin gene, and a second expression vector containing an expressible gene encoding for a desired protein. Also contemplated, and encompassed by the instant invention is a mammalian host cell for the expression of a desired protein in cell culture, wherein said host cell is transformed with an expression vector containing an expressible mammalian fetuin gene, and an expressible gene encoding for a desired protein.

The methods of the present invention also encompass the production of a desired protein from a cell culture wherein the cells of said cell culture are transformed with an expression vector containing an expressible fetuin gene, and wherein said cells also express a desired protein. Such methods also encompass the production of a desired protein from host cells which have been selected or otherwise manipulated for enhanced fetuin expression, and are expressing a desired protein.

In order to aid efficient transformation of host cells, it is contemplated that the methods of the invention include the use of a expression vector which also contains a gene which encodes for a selectable marker.

In a particular aspect, the invention encompasses the methods and host cells described above, wherein said expression vector containing a fetuin gene is the expression vector pSV-AHSG. One particular embodiment of the present invention are methods and host cells as described above wherein said expression vector containing a gene encoding for a desired protein is pCMGGF2, and said desired protein is human Glial Growth Factor 2 (GGF2).

In on particular embodiment, the invention encompasses the fetuin adapted host cell CHO-α2HSGP and progeny or derivatives thereof.

Thus, in a particular aspect, the invention specifically encompasses the nucleic acid sequence of the expression vector pSV-AHSG, and of expression vector pCMGGF2.

BRIEF DESCRIPTION OF THE FIGURES

The embodiments and constructs of the invention can be better understood with reference to the following figures in which.

DETAILED DESCRIPTION OF THE INVENTION

The present invention encompasses the unexpected discovery that mammalian host cells can be adapted for efficient protein expression of a first desired protein, by the transformation of the host cell for the production of a first protein, wherein said first protein is either alpha-2-HS-glycoprotein, or mammalian fetuin. The methods, constructs and host cells of the invention are suitable for production of desired protein in standard small-scale culture systems, as well as large-scale production systems, including and not limited to fermenter systems, hollow fiber culture systems, tumbler systems, and suspension culture systems.

Protocols and methods for the manipulation of nucleic acids, PCR amplification of nucleic acids, construction of expression vectors, transformation of host cells, and the culture of transformed cells for the production of protein are known in the art and can be found in a variety of laboratory manuals or texts, see generally Sambrook et al., 1989 *Molecular Cloning*, $2^{nd}$ edition, Cold Spring Harbor Press; Ausubel et al., 1992 *Short Protocols in Molecular Biology*, $2^{nd}$ edition, John Wiley & Son; *Gene Expression Technology*, Methods in Enzymology Vol. 185 (ed. David Goeddel et al., Academic Press, Inc., London, 1991); *Gene Structure and Expression*, $2^{nd}$ Edition, J. D. Hawkins (Cambridge University Press, London, 1991); *PCR Protocols: A Guide to Methods and Applications* (Innis, et al. 1990, Academic Press, San Diego, Calif.); *Culture of Animal Cells: A Manual of Basic Technique*, 2nd Ed. (R. I. Freshney. 1987, Liss, Inc. New York, N.Y.); *Methods in Molecular Biology* (Vol. 7), *Gene Transfer and Expression Protocols*, (ed. E. J. Murray, 1991, The Humana Press Inc., Clifton, N.J.); Ramsay, M., *Yeast Artificial Cloning*, 1994, Molec. Biotech. 1: 181–201; and, Smith, et al. 1990. *Amplification of large artificial chromosomes* Proc. Natl. Acad. Sci. U.S.A. 87: 8242–8246.

The invention and many of its aspects can be better understood by way of illustration in the following examples.

EXAMPLE 1

Fetuin Expression and Host Cells

Figure 1:
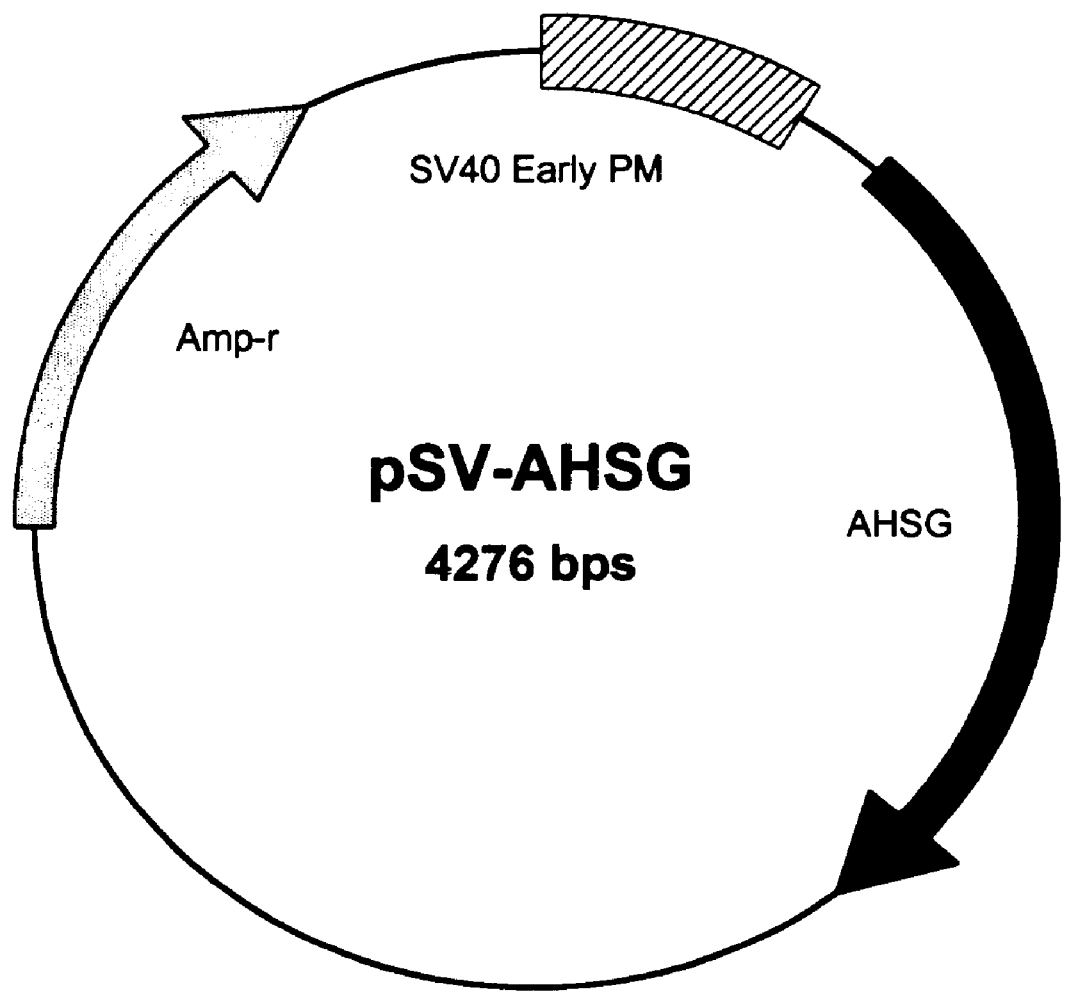
FIG. 1 is a diagram illustrating an expression vector for human alpha-2-HS-glycoprotein (expressing SEQ ID NO.: 5 encoding for a human fetuin ortholog protein SEQ ID NO.: 6), pSV-AHSG.

Using an expression vector suitable for transfection of mammalian cells, a nucleic acid sequence encoding for a human fetuin gene ortholog of SEQ ID. NO:5 was operably inserted and the complete vector transformed into CHO host cells. One example of a fetuin expression vector of the present invention is pSV-AHSG (FIG. 1). A suitable starting expression vector is one which would be suitable for accepting the insertion of a desired fetuin gene, such that it is operably linked to a suitable promoter/enhancer system. AHSG was cloned by reverse transcriptase-mediated PCR (RT-PCR) techniques using human liver MRNA (Clonetech, Palo Alto, Calif.). The sequence for the PCR primers were 1) 5'-CCT CCA ACC ACC TGC ACG CC (SEQ ID NO.: 7) and 2) 5'-GTG GCT ATG TTT TCT GTG CC (SEQ ID NO.: 8).

In order to allow for efficient selection and maintenance of stable transformation, the preferred suitable expression vector can contain one or more selectable marker gene, for example an antibiotic resistance gene, or otherwise required metabolic protein when paired with a suitably deficient host cell. In contemplated embodiments of the present invention, a suitable expression vector can contain a nucleic acid encoding any suitable mammalian fetuin, for example bovine fetuin, murine fetuin, porcine fetuin, equine fetuin or rat fetuin The nucleic acid sequences encoding for mammalian fetuin genes are known in the art and are available in the GenBank data bank, including Human (#36317), Rat BSP (#89822), Rat pp63 (#92482), Rat fetuin (#94301), Bovine fetuin (#101386), Ovis aries fetuin (#104788), and *S. scrofa* fetuin (#108394). Prefered fetuin genes are Human (#36317) (SEQ ID No. 3), and Bovine fetuin (#101386) (SEQ ID No. 1), their homologs and orthologs, such as for example the nucleic acid sequence of SEQ ID No. 5.

Suitable mammalian host cells are then transformed with a fetuin expression vector and selected for stable transfection. In a preferred embodiment, the starting host cells are CHO cells, and after transfection have the phenotype (dhfr$^-$/ α2HSGP).

Suitable host cell lines in which constitutive expression of fetuin occurs allows for enhanced protein expression from an expression vector. Constitutive expression of fetuin can be established by sequential transfection of host cells with an expression vector containing a fetuin gene; screening and selection for transformed cells expressing fetuin protein; then subsequent transfection of the selected cells (or progeny thereof) with an expression vector containing a gene or genes of the desired protein or proteins to be expressed.

A preferred method involves co-transfection of host cells with separate expression vectors, wherein one vector would encode for a fetuin gene, and the other vector or vectors would encode for one or more desired proteins. However, one of ordinary skill in the art would know how to construct combined expression vectors wherein a fetuin gene is expressed from the same vector as that encoding for and expressing one or more desired proteins. A further permutation of the invention would involve co-transfecting such a combined fetuin/protein expression vector with one or more additional expression vectors which encode for desired protein(s).

As one of ordinary skill in the are would recognize, several permutations of the present invention can be constructed and used without undue experimentation.

Once the transformed host cells are established, it is possible to further screen and select such transformed host cells for additional phenotypic properties such as protein expression level, growth rate, and growth conditions such as temperature, media requirements and suitability for growth in low-protein or serum-free media.

In particular, CHO cells can be transformed with plasmid pSV-AHSG to result in the fetuin adapted host cell called CHO-α2HSGP (CHO phenotype dhfr⁻/α2HSGP).

EXAMPLE 2

Recombinant human glial growth factor (GGF2)

Although the etiology of multiple sclerosis (MS) remains unknown, treatment strategies for this demyelinating disease have been based on the modulation of the immunological events that accompany the formation of MS lesions (Waubant E L, Oksenberg J R, and Goodkin D E. 1997. Pathophysiology of multiple sclerosis lesions. Science & Medicine 4: 32–41). Beta-interferon is one of the immuno-modulators that has been used successfully to treat relapsing forms of MS. Other factors such as mitogenic growth factors for oligodendrocytes have been identified as one of the emerging treatment strategies for MS. The therapeutic potential of these neurotrophic factors was surmised to promote remyelination. Recombinant human glial growth factor (GGF2) is one of these factors with documented stimulatory effects on Schwann cells and oligodendrocytes (Mahanthappa N K, Anton E S, and Matthew W D. 1996. Glial growth factor 2, a soluble neuregulin, directly increases Schwann cell motility and indirectly promotes neurite outgrowth. J. Neuroscience 16: 4673–4683). A method for the production of GGF2 for treatment of neurodegenerative disorders and demyelination in peripheral or central nervous system has been described in U.S. Pat. No. 5,530,109 (incorporated by reference in its entirety).

Using both the expression vector and production cell lines that were described in U.S. Pat. No. 5,530,109 their productivity was evaluated. To our surprise these cell lines have rather low specific productivity (0.5–1 pg/c/d) and are unstable. Subsequently we tried to derive high producing cell lines using this vector without success. The transfection efficiency was so low that selection in methotrexate yielded only one transformant out of 14 million cells.

In order to derive stable cell lines with high productivity for GGF2, an improved vector was constructed. Derivation of production cell lines was done in Chinese hamster ovary cells, CHO (dhfr⁻) and CHO (dhfr⁻/α2HSGP) cells using the improved vectors. Selection of high producing cells was done in various concentrations of methotrexate. Protein-free clones were derived by gradual weaning of cells from serum proteins. The specific productivity of these clones is in the range of 20–30 pg/c/d. Protein-free conditions can be defined as the absence of substantially all human and animal serum and plasma derived proteins in the culture media, where said proteins may be present in trace amounts, but still supplemented with human insulin. It is preferred that the supplemental insulin be recombinant human insulin.

EXAMPLE 3

Construction of GGF2 expression vectors

For efficient transcription, the EBV BMLF-1 intervening sequence (MIS, a 5'- intronic sequence; 5'-IS) was inserted immediately upstream of the GGF2 cDNA, and downstream of the promoter. Specific methods and examples of for the generation of vectors such as pSM97 is described in U.S. Pat. No. 5,854,021.

The MIS sequence was generated by polymerase chain reaction (PCR) amplification from Epstein-Barr virus (EBV) reading frame designated BMLF1. This MIS sequence encompasses DNA sequence from 84,105 to 84,262 of B95-8 Epstein-Barr virus including an intronic sequence from 84,122 to 84,227 of B95-8 EBV (Farrell, Advances in Viral Oncology, Vol. 8, ed. G. Klein, Raven Press, Ltd., New York, 1989; Genbank access #X00784).

Two PCR primers 1) 5'-GGATCGATAACTAGCAGCATTTCCT-3' (SEQ ID NO.: 9) and 2) 5'-GGGTTAACTTCCAGAATGTGGCTCT-3' (SEQ ID NO.: 10) have extended restriction enzyme sites for ClaI (ATCGAT) and HpaI (GTTAAC) at the 5' and 3' ends respectively, for amplification and subsequent directional cloning of the MIS fragment. Of course other suitable restriction sites can be designed.

Figures 4A, 4B:
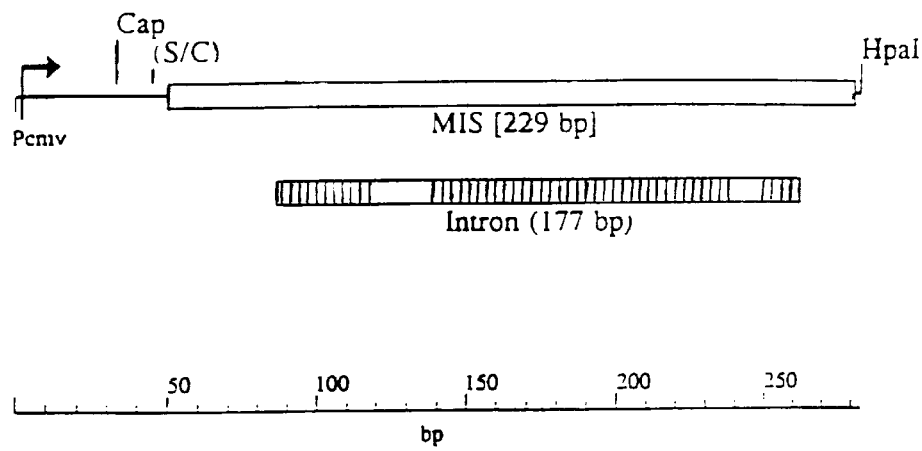
FIG. 4A shows a linear map of the CMV promoter, a 5'-intronic sequence (MIS), and HpaI cloning site. The parallel map shows the location of the 177 bp intron within the MIS sequence.
FIG. 4B shows the nucleotide sequence of MIS (SEQ ID NO.: 11). Denoted are the nucleotide sequence derived from EBV (bracketed) and its two donor-site (Open parenthesis signal) and one acceptor-site (close parenthesis signal). Two repeated sequences (2×71 bp) are underlined (thin and thick).

Using as a starting construct, expression vector pCIS-F8, having a stabilizing sequence (termed CIS) downstream of a promoter and upstream of the DNA encoding factor VIII (EP 0260148, published Sep. 17, 1987, incorporated by reference), the PCR MIS fragment, described above, digested with HpaI and ClaI was inserted into the ClaI/HpaI site of pCIS-F8 (after removal of the Factor VIII gene sequence). The resulting plasmid containing MIS was named pSM95. This MIS sequence (5'-IS) differs from the original EBV sequence by having an unexpected repeat of a 71 bp sequence which contains a donor site. This new MIS sequence (5'-IS, 229 bp) has two donor-sites and one acceptor-site. (See FIG. 4).

Figure 2:
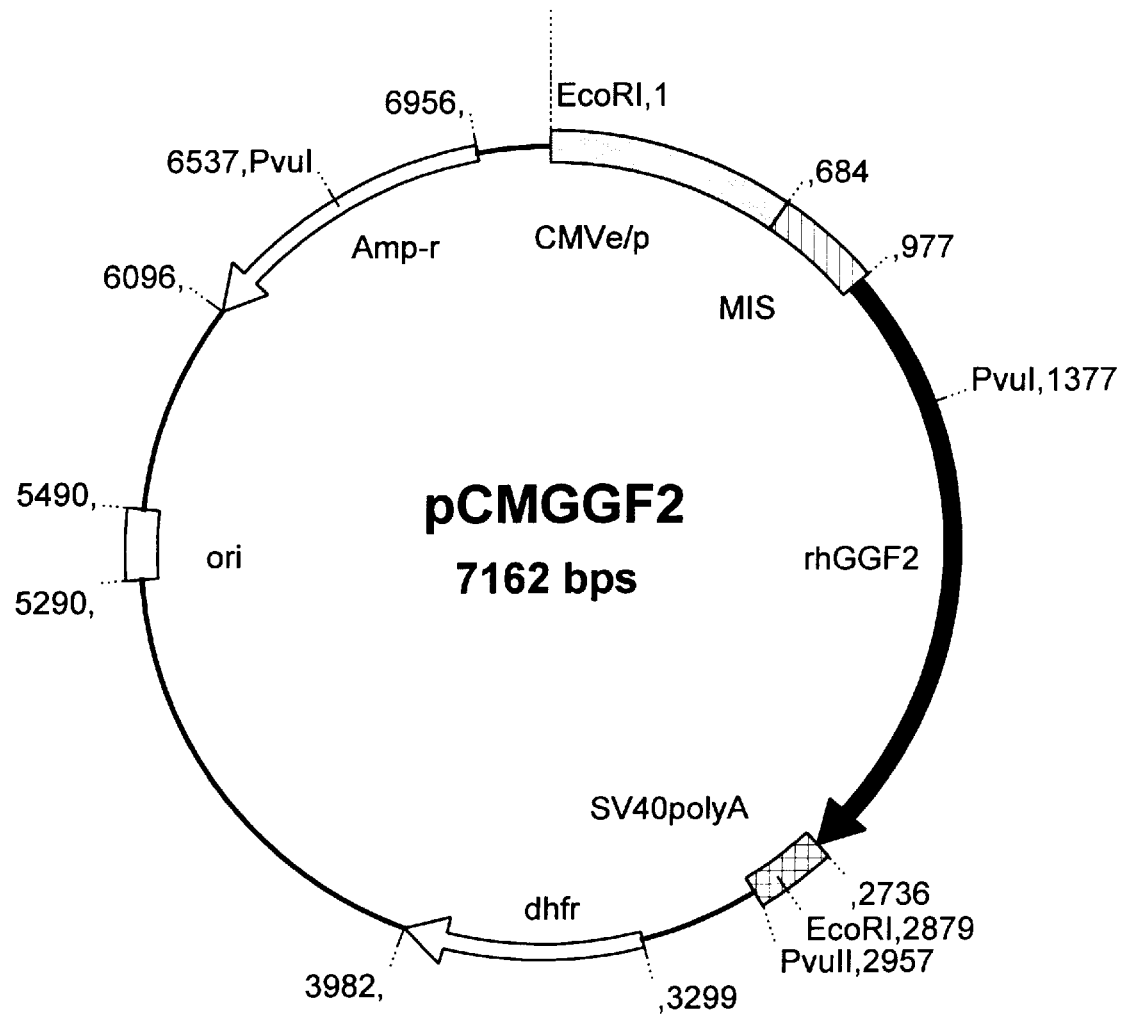
FIG. 2 is a diagram illustrating an improved GGF2 expression vector pCMGGF2.

The intronic sequence CIS was removed from pSM95 by SacII/ClaI digestion. The remaining backbone was blunt ended by Klenow and religated. This resulting plasmid, pSM97, consists of a CMV promoter/enhancer (CMVe/p), MIS, a unique HpaI site for cloning, a poly A signal, and a SV40 early promoter-dhfr in a plasmid backbone containing ori and amp$^r$ gene. Digestion of the plasmid pCGIG-HBS5 (U.S. Pat. No. 5,530,109) with EcoRI released the recombinant human GGF2 cDNA which was blunt-end ligated to the vector pSM97 at the unique HpaI site. The resulting construct is called pCMGGF2 (FIG. 2).

EXAMPLE 4

Derivation of GGF2 cell clones

Transfections.

CHO (dhfr⁻) and CHO (dhfr⁻/α2HSGP) cells were transfected with plasmid DNA using the cationic lipid DMRIE-C reagent (Life Technologies #10459-014). Triplicate wells of a 6-well plate were used for each plasmid DNA transferred into CHO (dhfr⁻) or CHO (dhfr⁻/α2HSGP). Briefly, in each well of a 6-well plate, 10 μl of DMRIE-C reagent was mixed with 2–5 μg of pCMGGF2 DNA in 0.5 ml of serum-free DMEM-F12 medium. The plate was incubated at room temperature for 30 minutes to allow formation of the lipid-DNA complexes. Subconfluent cells from one T-75 cm² flask were trypsinized with 0.5 ml 1× Trypsin-EDTA diluted in PBS (GibcoBRL #15400-054), stopped with 5 ml of growth medium, washed once with PBS, and resuspended in serum free DMEM-F12 medium to $10^7$ cells/ml. Then $2\times10^6$ logarithmically growing cells in 0.2 ml of serum-free medium was added to each well, followed by incubation of the plate for 4–5 hours at 37° C. in a $CO_2$ incubator. To each well, 2 ml of growth medium with 5% define FBS was added. The cells were assayed by ELISA at 48 to 72-hour post-transfection for transient expression.

Drug selection and gene amplification

Two to three days post transfection, cells from triplicate wells per transfection were trypsinized, pooled, and washed once with serum free medium. Viable cell densities were determined by the Trypan Blue exclusion method, then seeded in 96-well plates in 5% dialyzed FBS, 50 nM methothrexate selection medium. After screening for GGF2 secreting populations by ELISA, direct selection and amplification steps were carried out in increasing concentrations of methotrexate (100 nM, 200 nM, 400 nM, 1 μM) at 4–6 weeks intervals in a 6-well format with 3 ml of selection medium per well.

Limiting dilution cloning (LDC)

Single cell clones (SCC) were obtained by LDC at one cell in 200 μl medium per well of a 96-well format, in drug-free selection medium containing 1% dialyzed FBS. The cultures were fed once a week. After two weeks, the plates were scored for single cell growth by phase microscopy prior to ELISA screening.

Other suitable methods and constructs for selecting transfected cell lines for heterologous protein expression are described in the literature, and for example in U.S. Pat. No. 5,612,213.

GGF2 ELISA

A sandwich immunoassay for the detection of rhGGF2 in tissue culture supernatants was performed using standard procedures. (see generally Sambrook et al., 1989 *Molecular Cloning* $2^{nd}$ edition, Cold Spring Harbor Press; Ausubel et al., 1992 *Short Protocols in Molecular Biology*, $2^{nd}$ edition, John Wiley & Son; Rose et al., 1986 *Manual of Clinical Laboratory Immunology*, $3^{rd}$ edition, American Society of Microbiologists for suitable immunoassay protocols and methods.) On the addition of substrate, the amount of antibody antigen- peroxidase conjugated antibody complex can be measured by spectrophotometry. Samples can be compared against a standard curve of absorbance versus rhGGF2 concentration.

EXAMPLE 5

Protein-free Adaptation and Evaluation of Cell Clones

The selected GGF2 clones were weaned from 1% FBS by a stepwise twofold dilution in shake flask. Clone F10-B3, the highest producer with specific productivity of 20 pg/c/d, was protein-free adapted in a 1.5-liter fermenter using the basal production medium. The basal protein-free production medium is an enriched DMEM-F 12 medium, supplemented with 2 mM Glutamine, 100 μM $CaCl_2$, 250 μM L-Histidine, 50 μM $FeSO_4$/EDTA, 2 g/L $NAHCO_3$, 10 μg/ml recombinant human insulin, and 0.1% Pluronic F68 (Table 1). The medium maintains a pH range of 7.0–7.3 and an osmolarity range of 280–300.

TABLE 1

Transfection Efficiency of GGF2 Expression Vectors

| Plasmid | transfection efficiency | Sp. Productivity in protein-free |
|---|---|---|
| PCDIG-HBS5 | 1+/1,344 wells = 0.07% | 0.5–1.0 pg/c/d |
| PCMGGF2 | 320+/1,776 wells = 18.00% | 4.0–30.0 pg/c/d |

EXAMPLE 6

Production of GGF2

Figure 3:
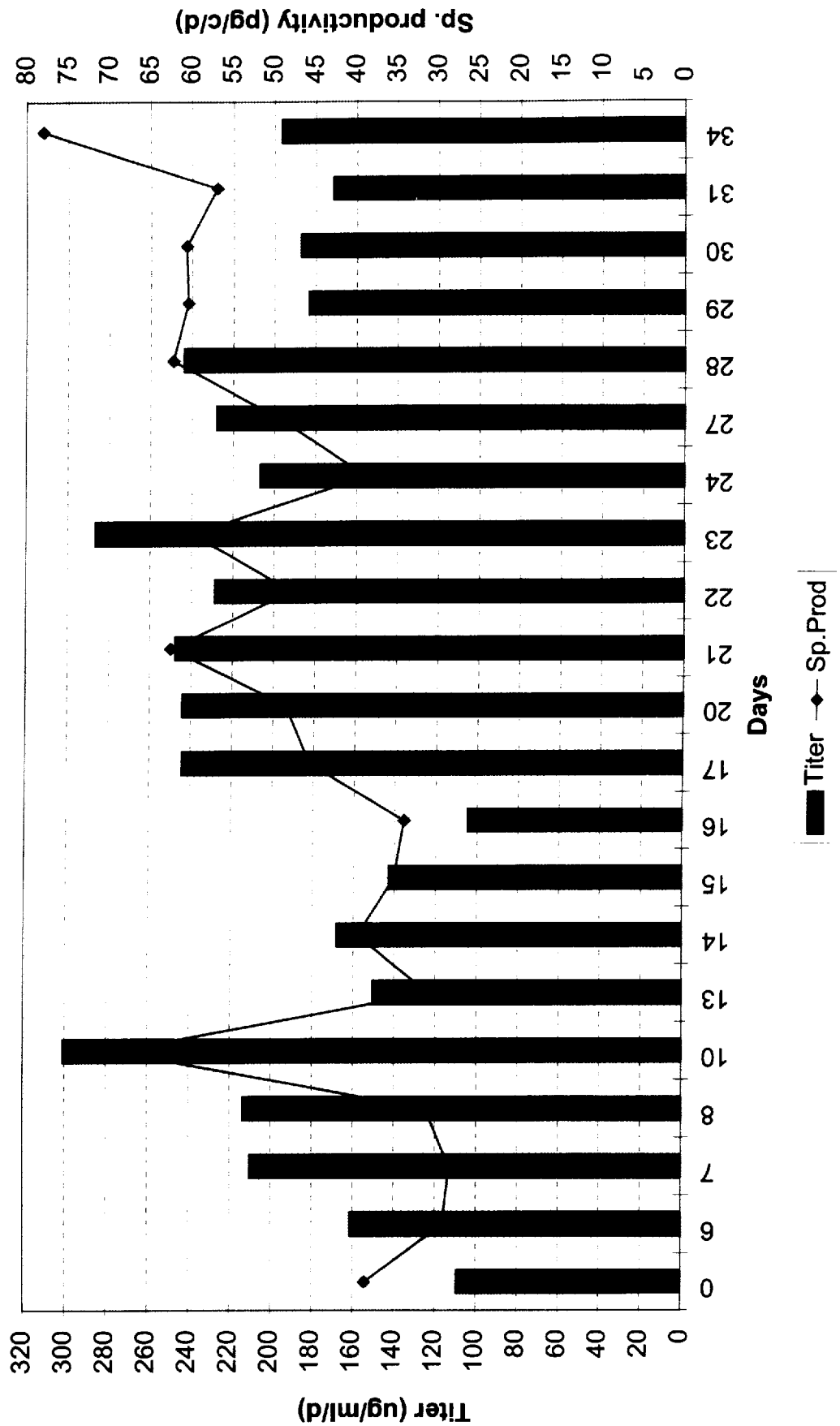
FIG. 3 is a chart which illustrates efficient protein-free production of GGF2 using a continuously perfused fermenter and CHO host cells transformed with the vector pCMGGF2.

A continuous protein-free production method for GGF2 was developed by seeding a 1.5-liter fermenter with clone F10-B3 cells using the basal production medium described above. The cell density of the fermenter was maintained at $\sim 2 \times 10^6$ cells/ml and perfused at a rate of 0.5 liter/day. As shown in FIG. 3, the cells continued to produce high levels of GGF2 throughout the 34-day production period. Titer as high as 240 mg/liter/day was observed. This continuous perfusion method can be easily adapted to large fermenters (200 to 500-liter) equipped with cell retention devices such as settlers. For example, using a 10-L fermenter, >40 g of GGF2 can be produced over a 60-day period using the methods and constructs of the present invention.

The prior art vector pCDIG-HBS5 described in U.S. Pat. No. 5,530,109 has very low transfection efficiencies. CHO (GGF2) clones generated by this vector not only have low specific productivity (0.5–1.0 pg/c/d) in serum free conditions but are also unstable. Surprisingly, the improved plasmid of the invention, pCMGGF2 supports stable and high expression of GGF2, and efficient selection and amplification of the dhfr gene under methotrexate selection and amplification. Clones derived with the improved vector display stable GGF2 expression and high specific productivity (20–30 pg/c/d) under protein-free conditions.

Productivity of various cell lines was further compared. Table 2 below compares the productivity of CHO and CHO-α2HSGP cells expressing GGF2 under serum-free conditions. Surprisingly the specific productivity of serum free clones adapted for fetuin expression were increased 2–8 fold higher than regular CHO cells.

TABLE 2

Enhanced Production of GGF2 in CHO Cells - Constitutive Expression of Fetuin

| Cell Line | Specific Productivity of GGF2 (average of 5 clones) |
|---|---|
| CHO (pCDIG-HBS5) | 0.5–1.0 pg/c/d |
| CHO (pCMGGF2) | 5–6 pg/c/d |
| CHO-AHSG (pCMGGF2) | 20–30 pg/c/d |

With certain embodiments of the invention being fully described, one of ordinary skill in the art will understand and be able to construct various equivalents of the present invention without departing from the spirit or scope of the present disclosure, in view of the claims below.

We claim:

1. A method for isolating a desired protein from a mammalian host cell, said method comprising transforming a mammalian host cell with an expression vector containing an expressible mammalian fetuin gene, transforming the same mammalian host cell with an expression vector containing an expressible gene which encodes said desired protein, expanding said transformed host cells in culture, and isolating said desired protein from said culture.

2. The method of claim 1 wherein said vector containing an expressible mammalian fetuin gene, or said expression vector containing an expressible gene which encodes said desired protein also contains a gene encoding a selectable marker.

3. The method of claim 1 wherein said expression vector containing an expressible mammalian fetuin gene also contains an expressible gene which encodes said desired protein.

4. The method of claim 3 wherein said expression vector contains a gene which encodes a selectable marker.

5. The method of claim 1 where said mammalian host cell is first transformed with an expression vector containing an expressible mammalian fetuin gene.

6. The method of claim 1 where said mammalian host cell is first transformed with an expression vector containing an expressible gene which encodes said desired protein.

7. A method for producing a transformed mammalian host cell that expresses a desired protein from a recombinant DNA expression vector in said transferred mammalian host cell, said method comprising transforming said mammalian host cell with an expression vector containing an expressible mammalian fetuin gene, and transforming the same mammalian host cell with an expression vector containing an expressible gene which encodes said desired protein.

8. The method of claim 7 wherein said vector containing an expressible mammalian fetuin gene, or said expression vector containing an expressible gene which encodes a desired protein also contains a gene encoding a selectable marker.

9. The method of claim 7 wherein said expression vector containing an expressible mammalian fetuin gene also contains an expressible gene which encodes said desired protein.

10. The method of claim 9 wherein said expression vector contains a gene which encodes a selectable marker.

11. The method of claim 7 where said mammalian host cell is first transformed with an expression vector containing an expressible mammalian fetuin gene.

12. The method of claim 7 where said mammalian host cell is first transformed with an expression vector containing an expressible gene which encodes said desired protein.

13. A mammalian host cell that expresses a desired protein in cell culture, wherein said host cell is transformed with an expression vector containing an expressible mammalian fetuin gene, and a second expression vector containing an expressible gene encoding said desired protein.

14. A mammalian host cell that expresses a desired protein in cell culture, wherein said host cell is transformed with an expression vector containing an expressible mammalian fetuin gene and an expressible gene encoding said desired protein.

15. The method of claim 2 wherein said expression vector containing an expressible mammalian fetuin gene is the expression vector pSV-AHSG.

16. The method of claim 2 wherein said expression vector containing an expressible gene which encodes said desired protein is pCMGGF2.

17. The mammalian host cell of claim 13, wherein said expression vector containing an expressible mammalian fetuin gene is the expression vector pSV-AHSG.

18. The mammalian host cell of claim 13 wherein said expression vector containing an expressible gene encoding said desired protein is pCMGGF2.

19. An expression vector comprising:

a) a promoter, b) a first coding sequence that encodes fetuin, said first coding sequence being operably linked to the promoter, c) an intronic sequence, the intronic sequence being downstream of the promoter and upstream of the fetuin coding sequence, the intronic sequence comprising two identical donor sites and one acceptor site, and d) a second coding sequence that encodes a desired protein, said second coding sequence being operably linked to a promoter.

20. The expression vector of claim 19 wherein said first coding sequence that encodes fetuin is either human, bovine, or a homolog or ortholog thereof.

21. An expression vector identified as pSV-AHSG.

22. An expression vector identified as pCMGGF2.

23. A host cell transformed by the expression vector of claim 21.

24. A host cell transformed by the expression vector of claim 22.

25. The host cell of claim 23 further transformed by the expression vector pCMGGF2.

* * * * *